US006423310B1

(12) United States Patent
Wilson et al.

(10) Patent No.: US 6,423,310 B1
(45) Date of Patent: Jul. 23, 2002

(54) BIOLOGICAL COATING WITH A PROTECTIVE AND CURATIVE EFFECT FOR THE CONTROL OF POSTHARVEST DECAY

(75) Inventors: Charles Wilson, Martinsburg, WV (US); Ahmed El Ghaouth, Frederick, MD (US)

(73) Assignees: Biotechnology Research and Development Corporation, Peoria, IL (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/324,524

(22) Filed: Jun. 2, 1999

Related U.S. Application Data

(60) Provisional application No. 60/088,302, filed on Jun. 5, 1998.

(51) Int. Cl.$^7$ .............................................. A01N 63/04
(52) U.S. Cl. ............................ 424/93.51; 435/255.1; 435/255.4; 435/255.5
(58) Field of Search ................... 424/93.51; 435/255.5, 435/255.2, 255.4, 255.1

(56) References Cited

U.S. PATENT DOCUMENTS

| | | | |
|---|---|---|---|
| 5,215,747 A | 6/1993 | Hairston et al. | 424/93 |
| 5,591,429 A | 1/1997 | Wilson et al. | 424/93.51 |
| 5,633,025 A | 5/1997 | Ghaouth et al. | 426/62 |
| 5,670,368 A | 9/1997 | McLaughlin et al. | |
| 5,830,459 A | * 11/1998 | Cuero | 424/93.4 |

FOREIGN PATENT DOCUMENTS

| | | | |
|---|---|---|---|
| JP | 60130346 | * | 7/1985 |
| WO | WO 92/18009 | | 10/1992 |
| WO | WO 94/17667 | | 8/1994 |
| WO | 94/19950 | * | 9/1994 |
| WO | WO 95/02964 | | 2/1995 |
| WO | WO 96/13985 | | 5/1996 |

OTHER PUBLICATIONS

Droby et al., Postharvest News and Information, 2:169–173, 1990.*

Droby, S. et al. (1997) "Influence of CaCl2 on penicillum digitatum, grapefruit peel tissue, and biocontrol activity of Pichia guilliermondii" *Phytopathology* 87: 310–315.

Freeman, A. and Dror, Y. (1994) "Immobilization of disguised yeast in chemically crosslinked chitosan beads" *Biotechnology and Bioengineering* 44: 1083–1088.

Allen, C.R. and Hadwiger, L.A. (1979) "The Fungicidal Effect of Chitosan on Fungi of Varying Cell Wall Composition" *Exp Mycol* 3: 285–287.

Düring, K. (1993) "Can Lysozymes Mediate Antibacterial Resistance in Plants?" *Plant Mol Biol* 23: 209–214.

Ghaouth, A. El et al (1991) "Chitosan Coating Effect on Storability and Quality of Fresh Strawberries" *J Food Sci* 56(6): 1618–1620

Ghaouth, A. El et al (1992) "Chitosan Coating to Extend the Storage Life of Tomatoes" *Hort Sci* 27(9): 1016–1018.

Ghaouth, A. El et al (1992) "Antifungal Activity of Chitosan on Post–Harvest Pathogens: Induction of Morphological and Cytological Alterations in *Rhizopus stolonifer*" *Mycol Res* 96(9): 769–779.

International Search Report (Dec. 10, 1999).

Manocha, M.S. and Govindsamy, V. (1997) "Chitinolytic Enzymes of Fungi and Their Involvement in Biocontrol of Plant Pathogens" *Plant–Microbe Interact and Biological Control* Marcel in Biocontrol of Plant Pathogens *Plant–Microbe Interact and Biological Control* Marcel Dekker, Inc. New York.

Mauch, F. et al (1998) "Antifungal Hydrolases in Pea Tissue" *Plant Physiol* 88: 936–942.

Robert, W.K. and Selitrennikoff, C.P. (1988) "Plant and Bacterial Chitinases Differ in Antifungal Activity" *J Gen Microbiol 134*: 169–176.

Wilson, C.L. and Ghaouth, A. El (1993) "Multifaceted Control of Postharvest Diseases of Fruits and Vegetables" *Amer Chem Soc* pp. 181–184.

* cited by examiner

*Primary Examiner*—Irene Marx
(74) *Attorney, Agent, or Firm*—Barnes & Thornburg; Alice O. Martin

(57) ABSTRACT

Novel methods and compositions are provided for the biocontrol of plant diseases by use of a biological coating that confers both a protective and a curative effect for the control of postharvest decay. The coating includes chitosan salts, an antagonistic microorganism, and a cation. A composition of chitosan salts, $CaCl_2$ and yeast is effective. The combined fungicidal activities of the chitosan salts and the antagonistic microorganism make the compositions of the present invention superior to previous coatings. When applied to the surface of a harvested plant commodity, the compositions both prevent and cure postharvest decay.

9 Claims, No Drawings

BIOLOGICAL COATING WITH A PROTECTIVE AND CURATIVE EFFECT FOR THE CONTROL OF POSTHARVEST DECAY

This application claims priority from co-pending application U.S. Provisional Serial No. 60/088,302 filed Jun. 6, 1998.

Novel methods and compositions are provided for the biocontrol of plant diseases by use of a biological coating that has both a protective and a curative effect for the control of postharvest decay. The coating includes chitosan salts, at least one antagonistic microorganism, and a softener.

BACKGROUND OF THE INVENTION

The U.S. market for biocontrol of tree fruit postharvest diseases could exceed $100 million by the year 2000 (*Industrial Bioprocessing*, September 1992). In *Postharvest News and Information* (1991) it was estimated that approximately 25% of harvested fruit and vegetables are lost because of postharvest diseases. Synthetic fungicides have been the primary means for controlling postharvest diseases of fruit and vegetables. However, increased concern of the public over the carcinogenicity of synthetic fungicides, has led to the withdrawal of some fungicides from the market. The development of fungicide-resistance in pathogens has limited chemical fungicides as a means of controlling them.

Control of plant diseases is not a problem confined to the U.S. The European Parliament has voted in favor of a total ban on postharvest treatment of fruits and vegetables with pesticides as soon as this ban becomes feasible. The withdrawal of current fungicides from use in the United States and other parts of the world is creating a large, new market for biological control agents ("biocontrol"). Baker (1987) has defined biological control as "the decrease of inoculum or the disease-producing activity of a pathogen accomplished through one or more organisms, including the host plant but excluding man." The cost of commercializing a biological control agent is much less expensive than the cost of commercializing a synthetic pesticide because only Tier 1 toxicology tests (Hofstein et al., 1994) are required. Also, if a biological control agent is properly selected, fewer new environmental impact studies are required.

Present coatings (mostly waxes) for postharvest commodities are somewhat effective in delaying ripening, but in general, do not prevent decay. Moreover, these coatings are under scrutiny as possible health hazards. Synthetic fungicides which have been added to the coatings to alleviate the problems of decay have recently been withdrawn from the market, and there is also public pressure to remove the petroleum-based coatings because of health and environmental concerns. A critical need therefore exists for alternatives to presently available coatings for agricultural commodities. The coatings need to be fungicidal as well as safe for the consumer and the environment.

Antagonistic yeasts have been reported to be effective agents for the biological control of postharvest diseases (Wilson and El Ghaouth, 1993). However, antagonistic microorganisms currently available have not been demonstrated to provide control of fruit and vegetable postharvest decay comparable to that obtained with synthetic fungicides. Limitations include the microorganisms' inability to cure previously-established infections in the crops and to prevent the resumption of quiescent infections.

Recently, chitosan, an animal-derived polymer, has been shown to have some potential as an antifungal preservative. Chitosan, a $\beta$-1,4-glucosamine polymer, is commercially produced from chitin of arthropod exoskeletons that have been deacetylated to provide sufficient free amino groups to render the polymer readily soluble in diluted organic acids. Chitosan and its derivatives are known to form a semipermeable film (Averbach, 1978), to be inhibitory to a number of pathogenic fungi (Allan and Hadwiger, 1979), and to activate a number of biological processes in plant tissues, including the stimulation of chitinases, the accumulation of phytoalexins, the synthesis of proteinase inhibitors, and increased lignification (El Ghaouth et al., 1992, a, b). The polycationic nature of chitosan is believed to provide the basis for its physico-chemical and biological functionality. Chitosan is regarded safe as indicated by feeding trials with domestic animals. When applied as a coating, chitosan controlled decay and delayed ripening of strawberry, bell pepper, tomato, and cucumber by acting as a selective barrier to gas diffusion (El Ghaouth et al., 1991). The control of decay by chitosan is believed to originate, in part, from its antifungal property. Indeed, in vitro studies showed that chitosan not only inhibited the radical growth of major postharvest pathogens, but also induced severe morphological alterations in *Rhizopus stolonifer* and *Botrytis cinerea*, as well as increased cellular leakage in both fungi, presumably by interfering with fungal plasma membranes (El Ghaouth et al., 1992 b).

Because infection of commodities such as fruit can occur either prior to harvest or during harvesting, an ideal biological control agent is expected to display both a protective and curative activity comparable to that observed with synthetic fungicides. Currently available antagonistic microorganisms do not appear to be able to control previously-established infections and are most effective when applied prior to infection by the pathogen.

New safe and effective means of controlling postharvest diseases are needed. The present invention provides such means.

SUMMARY OF THE INVENTION

The present invention is directed to unique compositions that are a combination of antifungal agents with antagonistic microorganisms and a softener. The invention also relates to methods of preventing and curing postharvest decay of plants caused by various pathogenic fungi, by applying the compositions of the invention to plants.

The combinations of the present invention form a "biological coating." In an embodiment of a composition of the present invention, the antagonistic microorganism is a yeast in particular *Candida saitoana* and the antifungal agents include chitosan salts amended with $CaCl_2$. Other suitable microorganisms include bacteria, for example *Pseudomonas syringae* and *Bacillus subtilis*. In a preferred embodiment, the biochemical additive are chitosan salts amended with $CaCl_2$ or chitosan propionate amended with $CaCl_2$, and a yeast, in particular *Candida saitoana*. Other suitable genera of yeast include Candida spp; Cryptococcus spp; Pichia spp; Debaryomyces spp; Bulleromyces spp; Sporobolomyces spp; and Rhodotorula spp.

Other suitable chitosan salts include chitosan acetate; chitosan sorbate; chitosan propionate; chitosan lactate; chitosan glutamate; chitosan benzoate.

A softener is an additive that renders the yeast resistant to the adverse effects of chitosan and organic acids. Monovalent and divalent cations of Ca, Mg, Zn, or K are suitable. The softener is not considered to affect the pathogen.

The combination of the antifungal property of chitosan salts e.g. chitosan acetate and the biocontrol activity of antagonistic microorganisms such as the yeast *C. saitoana*, wherein the yeast functions against the pathogen in the presence of chitosan salts amended with $CaCl_2$, provides improved consistency and efficacy in controlling postharvest decay. In addition, the combination of antagonistic yeast (*C. saitoana*) with chitosan salts amended $CaCl_2$ offers control of postharvest decay of fruit and vegetables superior to that obtained with antagonistic yeast alone or chitosan salts amended with $CaCl_2$ alone. This improvement is unexpected and synergism was demonstrated.

Native chitosan and organic acids (acetic; sorbic; propionic; and lactic) are known to inhibit the growth of yeasts such as Candida spp and filamentous fungi such as *Botrytis cinerea, Penicillium expansum* Link, and *Penicillium digitatum*. Thus it is expected that the combination of chitosan-organic acid with *C. saitoana* will adversely affect the biocontrol activity of the selected yeast. However, unexpectedly, the combination produced improved control of pathogenic fungi.

The combination of antagonistic yeast (*C. saitoana*) with chitosan salts (chitosan acetate) amended with $CaCl_2$ may be applied to harvested crops either before or after infection because the combination has both a protective and curative effect against major postharvest pathogens and offers a level of control of decay better than that of synthetic fungicides.

The complexity of the mode of action displayed by the combined agents of the present invention makes the development of pathogen resistance in the target plants more difficult and presents a highly complex disease deterrent barrier.

An aspect of the invention is a biological coating for agricultural commodities that includes, in amounts effective for biocontrol activity, chitosan salts, and at least one antagonistic microorganism effective for the biocontrol of postharvest diseases, and a softener that is, a monovalent or divalent cation, e.g. $CaCl_2$. The effective amount of chitosan salts is from about 10 µg/ml to about 500 µg/ml, preferably about 20 µg/ml to about 250 µg/ml, more preferably about 200 µg/ml. The effective amount of one antagonistic microorganism is about $10^7$ colony forming units to about $10^8$ colony forming units; preferably about $10^8$ colony forming units. Another aspect of the invention is a method of protecting a commodity against postharvest decay, which includes coating the surface of the commodity by spraying, dipping, or drenching with an effective amount of the biological coating.

Fruit and plants that are targets for the methods and compositions of the present invention include pome fruit (e.g., apple, pear); stone fruit (e.g. peach, nectarine, prune); citrus fruit (e.g., orange, lemon, grapefruit, tangerine); vegetables (e.g. tomato, bell pepper, cucumber); root crops (e.g., potato, carrots); tropical fruit (e.g., mango, banana, guava, pineapple, avocado); melon fruit.

DESCRIPTION OF THE PREFERRED EMBODIMENTS

The present invention provides a novel combination of chitosan salts with at least one microorganism that is antagonistic to postharvest pathogens, and a softener. Native chitosan is known to adversely affect the viability of both antagonistic yeasts and postharvest pathogens. This previous knowledge hindered the use of chitosan salts as a potential additive to biocontrol agents (such as antagonistic yeasts). However, the addition of divalent or monovalent cations (a "softener") such as $CaCl_2$ to the combination of chitosan-salts with *Candida saitoana* allowed the antifungal property of chitosan to be exploited and the biocontrol activity of the antagonistic yeast (*C. saitoana*) to be enhanced. Chitosan-salt formulation that acts as a carrier for an antagonistic microorganism, with a coating that delays ripening, is inhibitory to postharvest pathogens. For example, the addition of a softener such as $CaCl_2$ to the combination of chitosan-salts with *C. saitoana* allowed the antifungal property of chitosan and the biocontrol activity of *C. saitoana* to be exploited.

Chitosan salts; acetate; sorbate; propionate; lactate; and glutamate amended with $CaCl_2$ are inhibitory to postharvest pathogens such as *B. cinerea* and *P. expansum* but show no effect on the growth of *C. saitoana* (Table 1). This was further confirmed by the results obtained with apple fruit. Apple wounds treated with a combination of *C. saitoana* with chitosan salts amended with $CaCl_2$ showed an intense colonization of the wound by *C. saitoana* (Table 2). The complexities of this combination provide a unique composition (product). While yeasts which have been found effective include *Candida saitoana* (*C. saitoana*), *Candida oleophila* (*C. oleophila*), *Candida sake* (*C. sake*), *Candida tenius* (*C. tenius*), *Candida utilis* (*C. utilis*), *Pichia guilliermondii* (*P. guilliermondii*), it is well within the level of skill in the art to determine if a particular antagonistic microorganism shows the necessary resistance by combining the candidate microorganism with chitosan salts amended with $CaCl_2$ in culture and observing whether or not the microorganism remains viable and grows. The combination of chitosan salt-$CaCl_2$ with an antagonistic yeast (*C. saitoana*) offers effective control of a major postharvest rot of fruit and gives superior control over use of an antagonist or chitosan salts-$CaCl_2$ alone.

The combination of chitosan-acetate-$CaCl_2$ with *C. saitoana* was more effective in controlling decay of apple, orange, and lemon fruit (Table 3 and 4) than either the antagonist microorganism or chitosan-acetate-$CaCl_2$ alone. After 14 days of storage, 23% of the lemons treated with the combination of *C. saitoana* with chitosan-acetate-$CaCl_2$ and inoculated with *P. digitatum* were diseased (Table 4), while 75% and 35% of the fruit treated with 0.1% chitosan-acetate-$CaCl_2$ or *C. saitoana* and inoculated with *P. digitatum* were diseased. All of the control apples inoculated with *P. digitatum* alone were diseased. The same pattern of decay control by the combination was also observed in apple and orange fruit (Table 3 and 4). The beneficial effect of $CaCl_2$ is illustrated by the poor level of disease control obtained with the combination of *C. saitoana* with chitosan-acetate with $CaCl_2$ (Table 3).

In addition to preventing decay, the combination of *C. saitoana* with chitosan-acetate-$CaCl_2$ also displayed a curative activity against major pathogens of apple and citrus fruit (Table 5 and 6). In citrus fruit, the combination of *C. saitoana* with chitosan-acetate-$CaCl_2$ was very effective in controlling early infections caused by *P. digitatum*. The level of control observed with the combination of *C. saitoana* with chitosan-acetate-$CaCl_2$ was significantly higher than that obtained with either the antagonist or chitosan-acetate-$CaCl_2$ alone (Table 5). Similar control of established infection by the combination of chitosan-acetate-$CaCl_2$ was also observed with apple fruit inoculated with *P. expansum* (Table 6). The results from pilot trials showed that the combination of *C. saitoana* with chitosan-acetate-$CaCl_2$ also was effective in controlling decay of oranges. The level of disease control obtained with the combination was comparable to that obtained with the recommended fungicide Thiabendazole (Table 7).

The curative effect of the combination is a substantial improvement over the combination of *C. saitoana* with glycolchitosan or carboxymethylchitosan (U.S. Pat. No. 5,633,025). The combination of *C. saitoana* with glycolchitosan or carboxymethylchitosan provides only protection and has no effect on established infections that occur before treatment. Because infection of fruit can occur either prior to harvest or during harvesting, an ideal biological product is expected to display both a protective and curative activity comparable to that observed with synthetic fungicides. Currently available antagonistic microorganisms do not appear to be able to control previously-established infections and are most effective when applied prior to infection by the pathogen. The lack of curative activity has been identified as a major limitation of biological approaches. The combination of *C. saitoana* with chitosan salts in presence of $CaCl_2$ offers both a curative and protective activity against rot.

EXAMPLES

The following examples illustrate embodiments of the invention:

Example 1
Preparation of Chitosan, Pathogens, and Yeast

Chitosan was dissolved 1:1 (w/v) in various organic acids (acetic acid; sorbic acid; propionic acid; lactic acid; and glutamic acid). Ripe apples (cv. Red Delicious) were hand harvested at the Appalachian Fruit Research Station, Kearneysville, W.Va. Orange and lemon fruit were purchased and stored at 4° C. Fruit were sorted to remove any fruit with apparent injuries or infections. Cultures of *Botrytis cinerea, Penicillium expansum* Link, and *Penicillium digitatum* were maintained on potato dextrose agar (PDA). Spore suspensions were obtained by flooding 2-week-old cultures of *B. cinerea, P. digitatum,* and *P. expansum* with sterile distilled water containing 0.1% (v/v) Tween 80. Spore counts were determined with an hemacytometer, and spore concentration was adjusted to about $10^4$ conidia per ml for Penicillium and about $10^5$ conidia per ml to Botrytis with sterile distilled water. *C. saitoana* was grown at 27° C. for 48 h. Shake-flask cultures of nutrient-yeast broth were started with approximately $10^4$ CFU of yeast, and incubated on an orbital shaker set at 200 rpm for 48 h. Yeast cells were collected by centrifugation at 3000 g for 20 min, resuspended in sterile distilled water, and centrifuged. The resulting pellets were dispersed in sterile distilled water and the concentration of the yeast suspension was adjusted to $10^8$ CFU/ml.

Example 2
Effect of Chitosan Salts on the Growth of Yeast and Pathogens

Antifungal properties of chitosan salts (acetate; sorbate; propionate; lactate; and glutamate) against the pathogens *Botrytis cinerea* and *Penicillium expansum* were determined in a 24-well microtiter dish. 0.1% chitosan salts (acetate; sorbate; propionate; lactate; and glutamate) solutions containing 0.2% maltose extract broth and 0 or 0.5% $CaCl_2$ were autoclaved and 100 µl of the solution was dispensed into each well. Each well was inoculated with approximately five hundred spores of *B. cinerea* and *P. expansum*. Four replicates of eight wells were used for each fungus per treatment. Microtiter dishes were incubated in the dark at 24° C. Percent spore germination was determined after 24 hours by techniques known to those of skill in the art.

The effect of the various chitosan salts (acetate; propionate; lactate; and glutamate) in presence or absence of 0.5% $CaCl_2$ on the survival of *C. saitoana* in yeast maltose broth was evaluated. Fifth milliliter Erlenmeyer flasks containing 0.1% chitosan salts (acetate; sorbate; propionate; lactate; and glutamate) and 0.2% yeast maltose broth were amended with 0 or 0.5% $CaCl_2$ and autoclaved. Each flask was started with approximately $10^5$ CFU of yeast and the flasks were incubated on an orbital shaker set at 200 rpm. Samples were collected every day over a period of 5 days and dilution-plated in duplicate on yeast-maltose agar medium. The plates were incubated at 24° C. and colonies were counted after 48 h.

The effect of the various chitosan salts (acetate; sorbate; and propionate) in the presence of 0.5% $CaCl_2$ on the survival of *C. saitoana* in apple wounds also was determined. Fruit were wounded, treated with cell suspensions of *C. saitoana* in 0.1% chitosan salts (acetate; sorbate; and propionate) containing 0.5% $CaCl_2$, and stored at 24° C. There were four replicates of five fruit per treatment with complete randomization and samples were collected after 7 days from two replicate fruit per treatment. Wound tissue was scraped with a sterile inoculating needle. The dislodged material was suspended in 10 ml of sterile water, macerated with a glass rod, vortexed, dilution-plated in triplicate on yeast-maltose agar medium, and the plates were incubated 24° C. Colonies were counted after 48 h. Chitosan salts amended with $CaCl_2$ were inhibitory to postharvest pathogens. A complete inhibition of spore germination of *B. cinerea* and *P. expansum* was observed with 0.1% chitosan salts (acetate; propionate; lactate; and glutamate) amended with 0.5% $CaCl_2$. Tables 1 and 2 show that the growth of antagonistic yeast, *C. saitoana* was not affected by chitosan salts amended with $CaCl_2$.

Example 3
Control of Decay by the Combination of Chitosan-salts and $CaCl_2$ with Yeast Yeast cells from 48 h old cultures of *C. saitoana* were pelleted by centrifugation, resuspended in sterile distilled water, and centrifuged. Pellets were suspended in 0.1% chitosan salt (chitosan-acetate) containing 0.5% $CaCl_2$ and the concentration of the yeast suspension was adjusted to $10^8$ CFU/ml. Apple, orange, and lemon fruit were individually wounded. To determine the protective activity of the combination, fruit wounds were first treated with one of the following treatments:

yeast cell suspension;

yeast cell suspension containing 0.1% chitosan-acetate and 0 or 0.5% $CaCl_2$;

0.1% chitosan-acetate containing 0 or 0.5% $CaCl_2$;

control—sterile water

Fifty microliters of a treatment was placed in a wound and thereafter the wounds were challenge-inoculated with 20 µl of a spore suspension of a pathogen. The fruit were incubated at 24° C. in plastic trays at high relative humidity (about 95% or above). Apple wounds were challenge-inoculated with *P. expansum*, while orange and lemon wounds were challenge-inoculated with *P. digitatum*. For each treatment, 20 to 100 fruit were arranged in a randomized complete block design (Steele and Torrie, 1968). Lesion diameter and percent infection were determined for each treatment after 7 days of storage and the tests were repeated twice.

Additional tests with apple, lemon, and orange fruit were also done to determine the curative activity of the combination. Apple wounds were inoculated with *P. expansum*, while orange and lemon wounds were challenge-inoculated with *P. digitatum*. After 24 hours of incubation at 24° C., inoculated wounds were treated with the different treatments as disclosed above. The fruit were incubated at 24° C. in plastic trays at high humidity. For each treatment, 20 to 100 fruit were arranged in a randomized complete block design. Lesion diameter and percent infection were determined for each treatment after 7 days of storage and the tests were repeated twice.

Results of the protective effect on decay of apple, orange, and lemon are shown in Tables 3 and 4. The combination of chitosan-acetate-$CaCl_2$ with *C. saitoana* was more effective in controlling decay of apple, orange, and lemon fruit (Tables 3 and 4) than either the antagonist or chitosan-acetate-$CaCl_2$ alone. After 14 days of storage, 23% of the lemon treated with the combination of *C. saitoana* with chitosan-acetate-$CaCl_2$ and inoculated with *P. digitatum* were diseased (Table 4). While 75% and 35% of the fruit treated with 0.1% chitosan-acetate-$CaCl_2$ or *C. saitoana* and inoculated with *P. digitatum* were diseased. All of the control apples inoculated with *P. digitatum* alone were diseased. The same pattern of decay control by the combination was also observed in apple and orange fruit (Tables 3 and 4). The beneficial effect of $CaCl_2$ is illustrated by the poor level of disease control obtained with the combination of *C. saitoana* with chitosan-acetate without $CaCl_2$ (Table 3).

The lack of curative activity has been identified as a major limitation of biological approaches. Microbial biocontrol agents are expected to display curative activity comparable to that observed with synthetic fungicides. The results in Tables 5 and 6 show chitosan-acetate-$CaCl_2$ also displayed a curative activity against major pathogens of apple and citrus fruit. In citrus fruit, the combination of *C. saitoana* with chitosan-acetate-$CaCl_2$ was very effective in controlling early infections caused by *P. digitatum* (Table 5). Similar control of established infection by the combination of *C. saitoana* with chitosan-acetate-$CaCl_2$ was also observed with apple fruit inoculated with *P. expansum* (Table 6). The observed curative activity of the combination shows the synergy between the antagonist and chitosan-acetate-$CaCl_2$.

The effect of the combination of chitosan-salt-$CaCl_2$ with yeast on natural infection of citrus fruit was also assessed under semi-commercial conditions that simulate commercial processes for fruit and vegetables but on a smaller scale. Orange fruit from field bins was washed on line following standard commercial practices (Standard Pre Chlorine wash; size and color blemish sorting; and randomized). Thereafter, the fruit were washed and treated with the different treatments using an on line spray system. Each treatment consist of at least 8 to 13 boxes of fruit; each box representing a replicate of approximately 60 to 100 fruit. The fruit were held at 50–55° F. and the percentage of decay was determined after 3 weeks. The results from pilot trials showed that the combination of *C. saitoana* with chitosan-acetate-$CaCl_2$ was effective in controlling decay of orange. The level of disease control obtained with the combination was comparable to that obtained with the recommended fungicide Thiabendazole (Table 7).

The addition of $CaCl_2$ renders other antagonistic yeasts besides *C. saitoana* such as *Debaryomyces hansenii; Cryptococcus laurentii; Candida sake; Candida oleophila; Candida orientalis; Zygosaccharomyces bisporus; Dekkera bruxellensis; Dekkera naardensis; Pichia angusta* resistant to native chitosan and organic acids used as solvents for chitosan. (Table 8)

TABLE 1

Survival of *Candida saitoana* in different chitosan-salts

| | Yeast cell Counts (CFU/ml) | |
|---|---|---|
| Treatment[a] | 0 days | 5 days |
| 0.1% Chitosan-glutamate | $1.8 \times 10^5$ | $1.8 \times 10^2$ |
| 0.1% Chitosan-glutamate + 0.5% $CaCl_2$ | $2.0 \times 10^5$ | $2.5 \times 10^4$ |
| 0.1% Chitosan-propionate | $1.8 \times 10^5$ | 0 |
| 0.1% Chitosan-propionate + 0.5% $CaCl_2$ | $2.2 \times 10^5$ | $2.6 \times 10^4$ |
| 0.1% Chitosan-lactate | $2.1 \times 10^5$ | 9 |
| 0.1% Chitosan-lactate + 0.5% $CaCl_2$ | $2.2 \times 10^5$ | $2.8 \times 10^4$ |
| 0.1% Chitosan-Acetate | $2.0 \times 10^5$ | 0 |
| 0.1% Chitosan-Acetate + 0.5% $CaCl_2$ | $2.2 \times 10^5$ | $2.8 \times 10^4$ |

[a]Chitosan-salt solutions containing 0 or 0.5% $CaCl_2$ were inoculated with $10^5$ yeast cells per ml and the solutions were stored at room temperature. Yeast survival was determined at different times over a period of 7 days.

TABLE 2

Survival of *Candida saitoana* in the presence of different chitosan salts

| Treatment[a] | Yeast cell Counts (CFU/ml) 7 days |
|---|---|
| *C. saitoana* alone | $3.7 \times 10^6$ |
| *C. saitoana* + 0.1% Chitosan-propionate + $CaCl_2$ | $3.1 \times 10^6$ |
| *C. saitoana* + 0.1% Chitosan-sorbate + $CaCl_2$ | $3.3 \times 10^6$ |
| *C. saitoana* + 0.1% Chitosan-Acetate + $CaCl_2$ | $3.4 \times 10^6$ |

[a]Apple wounds were treated with combination of yeast cells with different chitosan-salts and $CaCl_2$ and the fruit were stored at room temperature. Yeast survival was determined after 7 days of storage.

TABLE 3

Protective effect of the combination of *Candida saitoana* with chitosan-acetate formulations on decay of apple fruit caused by *Penicillium expansum*.

| Treatment[a] | Infected fruit (%)[b] *P. expansum* |
|---|---|
| Control | 78a |
| 0.1% Chitosan-Acetate | 82a |
| 0.1% Chitosan-Acetate +*C. sailoana* | 82a |
| *C. saitoana* | 47b |
| 0.1% Chitosan-Acetate + 0.5% $CaCl_2$ + *C. saitoana* | 30c |

[a]Apple wounds were treated with different treatments and then challenge-inoculated with 20 μl of *Penicillum expansum* at $10^4$ conidia per milliliter. Fruit were evaluated for symptoms of decay after 7 days of storage at 24° C.
[b]Columns with the same letter are not significantly different according to Duncan's multiple range test, P = 0.05.

TABLE 4

Protective effect of the combination of *Candida saitoana* with chitosan-acetate $CaCl_2$ formulation on decay of orange and lemon fruit caused by *Penicillium expansum*.

| | Infected fruit (%)[b] | |
|---|---|---|
| Treatment[a] | Lemon | Orange |
| 0.1% Chitosan-Acetate + 0.5% $CaCl_2$ | 100a | 100a |
| *C. saitoana* | 75b | 66b |
| 0.1% Chitosan-Acetate + 0.5% $CaCl_2$ *C. saitoana* | 35c | 33c |

TABLE 4-continued

Protective effect of the combination of *Candida saitoana* with chitosan-acetate CaCl₂ formulation on decay of orange and lemon fruit caused by *Penicillium expansum*.

| Treatment[a] | Infected fruit (%)[b] | |
|---|---|---|
| | Lemon | Orange |

[a]Orange and lemon wounds were treated with the difrerent treatments and then challenge-inoculated with 20 μl of *P. digitatum* at $10^4$ conidia per milliliter. Fruit were evaluated for symptoms of decay after 7 days of storage at 24° C.
[b]Columns with the same letter are not significantly different according to Duncan's multiple range test, P = 0.05.

TABLE 5

Curative effect of the combination of *Candida saitoana* with chitosan-acetate CaCl₂ formulation on decay of orange and lemon fruit caused by *Penicillium expansum*.

| Treatment[a] | Infected fruit (%)[b] | |
|---|---|---|
| | Lemon | Orange |
| Control | 100a | 100a |
| C. saitoana | 100a | 100a |
| 0.1% Chitosan-Acetate + 0.5% CaCl₂ | 75b | 66b |
| 0.1% Chitosan-Acetate + 0.5% CaCl₂ + C. saitoana | 23c | 20c |

[a]Orange and lemon wounds were challenge inoculated with 20 μl of *P. digitatum* at $10^4$ conidia per milliliter and 24 hours later, inoculated wounds were treated with tbe different treatments. Fruit were evaluated for symptoms of decay after 7 days of storage at 24° C.
[b]Columns with the same letter are not significantly different according to Duncan's multiple range test, P = 0.05

TABLE 6

Curative effect of the combination of *Candida saitoana* with chitosan-acetate CaCl₂ formulation on decay of apple fruit caused by *Penicillium expansum*.

| Treatment[a] | Infected fruit (%)[b] P. expansum |
|---|---|
| Control | 72a |
| C. saitoana | 72a |
| 0.1% Chitosan-Acetate + 0.5% CaCl₂ + C. saitoana | 39b |

[a]Apple wounds were challenge inoculated with 20 μl of *P. expansum* at $10^4$ conidia per milliliter and 24 hours later, inoculated wounds were treated with different treatments. Fruit were evaluated for symptoms of decay after 7 days of storage at 24° C.
[b]Columns with the same letter are not significantly different according to Duncan's multiple range test, P = 0.05.

TABLE 7

Effect of the combination of *Candida saitoana* with chitosan-acetate CaCl₂ formulation on natural infection of orange fruit.

| Treatment[a] | Infected fruit (%)[b] |
|---|---|
| Control | 5.2a |
| 0.1% Chitosan-Acetate + 0.5% CaCl₂ + C. saitoana | 1.8a |
| Thiabendazole (1000 ppm) | 1.4b |

TABLE 7-continued

Effect of the combination of *Candida saitoana* with chitosan-acetate CaCl₂ formulation on natural infection of orange fruit.

| Treatment[a] | Infected fruit (%)[b] |
|---|---|

[a]Valencia Oranges were treated within 48 hr after harvest under semi-commercial conditions using a processing line. Oranges from field bins were washed on line following standard commercial practices and then treated with water, yeast suspension containing 0.1% chitosan-acetate +0.5% CaCl₂, or Thiabendazole using an on line spray system. Each treatment consists of at least 8–13 boxes of fruit; each box representing a replicate of 60–100 fruit. The percentage of decay was determined after 3 weeks.
[b]Columns with the same letter are not significantly different according to Duncan's multiple range test, P = 0.05.

TABLE 8

Survival of different antagonistic yeasts in 0.1% chitosan-acetate containing calcium chloride.

| | Yeast Cell Counts (CFU/ml) | |
|---|---|---|
| Treatments | YMB | Chitosan-acetate + 5% CaCl₂ |
| C. orientalis | $1.1 \times 10^6$ | $1.3 \times 10^4$ |
| Z. bisporus | $1.1 \times 10^5$ | $5.7 \times 10^4$ |
| D. bruxellensis | $1.1 \times 10^5$ | $1.7 \times 10^4$ |
| D. naardensis | $1.6 \times 10^5$ | $6.3 \times 10^4$ |
| P. angusta | $4.0 \times 10^5$ | $7.0 \times 10^4$ |

Chitosan-acetate solutions containing CaCl₂ were inoculated with $10^5$ yeast cells per ml and the solutions were stored at room temperature. Yeast survival was determined after 3 days. The following yeasts were tested: *Candida orientalis*; *Zygosaccharomyces bisporas*; *Dekkera bruxellensis*; *Dekkera naardensis*; *Pichia angusta*.

DOCUMENTS CITED

Averbach, B. L. (1978) *Proc. 1st Int. Conf. Chitin and Chitosan*, R. A., and Pariser, E. R., eds., MIT, Cambridge, pp. 199.
Allan, C. R. and Hadwiger, L. A. (1979) *Exp. Mycol.*, 3:285–287;
Baker, K. F. (1987) *Ann. Rev. Phytopath.* 25:67–85.
El Ghaouth, A., Arul, J., Ponnampalam, R. & Boulet, M. (1991) *Journal of Food Science* 56:1618–1620 & 1631.
El Ghaouth, A. et al. (1992a) *Hortscience* 27:1016–1018.
El Ghaouth, A. et al. (1992b) *Mycol. Res.* 96:(9) 769–779.
Hofstein, R. S., Droby, S., Chalutz, E., Friedlander, T. (1994) In: Wilson, C. L., Wisniewski, M. E. (eds.) *Biological Control of Postharvest Diseases of Fruits and Vegetables*. CRC Press, pp. 89–100.
*Industrial Bioprocessing* (1992).
Mauch et al. (1988) *Plant Physiol*, 88:936–942.
*Postharvest News & Information* (1991).
Roberts, N. K. and Selitrennikoff (1988) *Journal of General Microbiology*, 134:169–176.
Steele, R. D. and Torrie, J. N. (1960) *Principles and Procedures of Statistics*, McGraw-Hill, New York, N.Y.
Wilson, C. L. and El Ghaouth, A. (1993) *Symposium Proceeding*. Beltsville Symposium XVIII.
U.S. Pat. No. 5,633,025.

We claim:

1. A biological coating for plants, said coating comprising, in amounts effective for biocontrol activity, chitosan salts, wherein the effective amount of chitosan salts is from about 10 μg/ml to about 500 μg/ml, an antagonistic yeast effective for the biocontrol of postharvest diseases, and CaCl₂ to render the yeast resistant to the adverse effects of chitosan salts.

2. The biological coating of claim 1, wherein the effective amount of chitosan salts is about 20 µg/ml to about 500 µg/ml.

3. The biological coating of claim 2, wherein said effective amount of chitosan salts is about 200 µg/ml.

4. The biological coating of claim 1, wherein the yeast is selected from the genera Candida, Cryptococcus, Pichia, Debaryomyces, Bulleromyces, Sporobolomyces, Rhodotorula, Aureobasidium, Zygosaccharomyces, and Dekkera.

5. The biological coating of claim 1, wherein the yeast is selected from a species in the genus Candida said species selected from the group consisting of *Candida oleophila, Candida saitoana, Candida sake, Candida tenius, Candida utilis* and *Pichia guilliermondii*.

6. The biological coating of claim 5, wherein the yeast is *Candida oleophila* or *Candida saitoana*.

7. The biological coating of claim 5, wherein the effective amount of the antagonistic yeast is about $10^7$ colony forming units to about $10^8$ colony forming units.

8. The biological coating of claim 7, wherein said effective amount of said antagonistic yeast is about $10^8$ colony forming units.

9. The biological coating of claim 1, wherein the chitosan salts are selected from a group consisting of acetate, sorbate, propionate, lactate and glutamate.

* * * * *

UNITED STATES PATENT AND TRADEMARK OFFICE
CERTIFICATE OF CORRECTION

PATENT NO. : 6,423,310 B1
DATED : July 23, 2002
INVENTOR(S) : Wilson et al.

It is certified that error appears in the above-identified patent and that said Letters Patent is hereby corrected as shown below:

Title page,
Item [56], OTHER PUBLICATIONS, "Ghaouth, A. EL e t al.", add a (period) -- . -- after "1620"

Column 1,
Line 7, please change "6" to -- 5 --

Column 3,
Line 6, add -- with -- after "AMENDED"

Column 5,
Line 67, please change "Fifth" to -- Fifty --

Column 6,
Line 57, please change "1968" to -- 1960 --

Column 7,
Line 50, please change "consist" to -- consists --

Column 8,
Table 2, please change "106" to -- $10^6$ --
Table 3, first column indicating Treatment, third row, please change "sailoana" to -- saitoana --

Column 9,
Table 5, under footnote a, please change "challenge inoculated" to -- challenge-inoculated --
Table 5, under footnote a, please change "tbe" to -- the --

Column 10,
Table 8, third column heading, please change "+5%" to -- 0.5% --
Table 8, fourth line in paragraph, please change "bisporas" to -- bisporus --

UNITED STATES PATENT AND TRADEMARK OFFICE
CERTIFICATE OF CORRECTION

PATENT NO.    : 6,423,310 B1
DATED         : July 23, 2002
INVENTOR(S)   : Wilson et al.

It is certified that error appears in the above-identified patent and that said Letters Patent is hereby corrected as shown below:

<u>Column 12,</u>
Line 10, please change "a" to -- the --

Signed and Sealed this

Twenty-fifth Day of November, 2003

JAMES E. ROGAN
*Director of the United States Patent and Trademark Office*